United States Patent
Lee et al.

(10) Patent No.: US 9,950,071 B2
(45) Date of Patent: Apr. 24, 2018

(54) HYBRID ANTICANCER PRODRUG SIMULTANEOUSLY PRODUCING CINNAMALDEHYDE AND QUINONE METHIDE AND METHOD FOR PREPARING SAME

(71) Applicants: INDUSTRIAL COOPERATION FOUNDATION CHONBUK NATIONAL UNIVERSITY, Jeollabuk-do (KR); KOREA RESEARCH INSTITUTE OF BIOSCIENCE AND BIOTECHNOLOGY, Daejeon (KR)

(72) Inventors: Dong Won Lee, Jeonju-si (KR); Byoung Mog Kwon, Yuseong-gu Daejeon (KR); Joung Youn Noh, Jeonju-si (KR); Byeng Su Kwon, Jeonju-si (KR); Dong Cho Han, Yuseong-gu Daejeon (KR)

(73) Assignee: Industrial Cooperation Foundation Chonbuk National University, Jeollabuk-Do (KR)

( * ) Notice: Subject to any disclaimer, the term of this patent is extended or adjusted under 35 U.S.C. 154(b) by 0 days.

(21) Appl. No.: 15/109,621

(22) PCT Filed: Jan. 5, 2015

(86) PCT No.: PCT/KR2015/000067
§ 371 (c)(1),
(2) Date: Sep. 30, 2016

(87) PCT Pub. No.: WO2015/102448
PCT Pub. Date: Jul. 9, 2015

(65) Prior Publication Data
US 2017/0014518 A1 Jan. 19, 2017

(30) Foreign Application Priority Data

Jan. 3, 2014 (KR) ........................ 10-2014-0000653
Jan. 5, 2015 (KR) ........................ 10-2015-0000660

(51) Int. Cl.
| | | |
|---|---|---|
| C07D 319/06 | (2006.01) |
| A61K 31/357 | (2006.01) |
| A61K 47/48 | (2006.01) |
| A61K 31/69 | (2006.01) |
| A61K 9/00 | (2006.01) |
| A61K 9/08 | (2006.01) |
| A23L 33/10 | (2016.01) |
| A23L 33/15 | (2016.01) |
| A23L 33/155 | (2016.01) |
| A23L 33/16 | (2016.01) |
| A61K 47/26 | (2006.01) |
| A61K 9/16 | (2006.01) |
| A61K 9/20 | (2006.01) |
| C07F 5/02 | (2006.01) |
| A61K 47/55 | (2017.01) |

(52) U.S. Cl.
CPC ............ *A61K 47/481* (2013.01); *A23L 33/10* (2016.08); *A23L 33/15* (2016.08); *A23L 33/155* (2016.08); *A23L 33/16* (2016.08); *A61K 9/0019* (2013.01); *A61K 9/08* (2013.01); *A61K 9/1611* (2013.01); *A61K 9/1623* (2013.01); *A61K 9/1652* (2013.01); *A61K 9/2018* (2013.01); *A61K 9/2059* (2013.01); *A61K 31/69* (2013.01); *A61K 47/26* (2013.01); *A61K 47/55* (2017.08); *C07F 5/025* (2013.01); *A23V 2002/00* (2013.01)

(58) Field of Classification Search
None
See application file for complete search history.

(56) References Cited

FOREIGN PATENT DOCUMENTS

| WO | WO-2000/33858 | 6/2000 |
| WO | WO 2000/33858 A1 * | 6/2000 |
| WO | WO-2005/65361 | 7/2005 |

OTHER PUBLICATIONS

Cornelison, TL. Human papillomavirus genotype 16 vaccines for cervical cancer prophylaxis and treatment. Curr. Opin. Oncol. 2000, vol. 12(5), p. 466.*
Burger, AM. Preclinical Screening for New Anticancer Agents. Springer. 2014, p. 23.*
Dunn, PJ. et al. Green Chemistry Principle #8. ACS What is Green Chemistry. Accessed from ACS Website on Jan. 8, 2016.*
International Preliminary Report on Patentability for PCT/KR2015/000067, dated Jul. 5, 2016, 7 pages.
International Search Report and Written Opinion for PCT/KR2015/000067, dated Apr. 24, 2015, 11 pages.
Hong et al., "Cinnamaldehydes in Cancer Chemotherapy," Phytotherapy Research (2016) 30:754-767.

* cited by examiner

*Primary Examiner* — Zinna Northington Davis
(74) *Attorney, Agent, or Firm* — Morrison & Foerster LLP

(57) ABSTRACT

The present invention relates to a hybrid anticancer prodrug simultaneously producing cinnamaldehyde and quinone methide. The hybrid anticancer prodrug according to the present invention sequentially releases quinone methide and cinnamaldehyde by $H_2O_2$ and acidic pH, and thus alkylates antioxidant GSH through the release of quinone methide, thereby inhibiting an antioxidative system and increasing oxidation stress, and generates and accumulates reactive oxygen species (ROS) through the release of cinnamaldehyde, thereby promoting apoptosis, and thus the hybrid anticancer prodrug according to the present invention can be favorably used as an anticancer drug by creating a synergetic anticancer effect through double stimulus-response and sequential treatment action in a cancer cell-specific manner.

15 Claims, 10 Drawing Sheets

[Fig. 1]
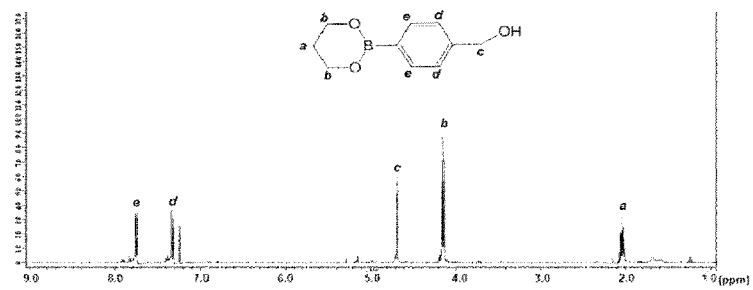
[Fig. 2]
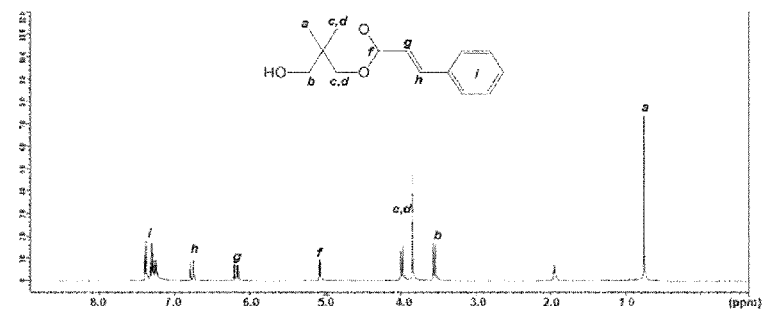
[Fig. 3]
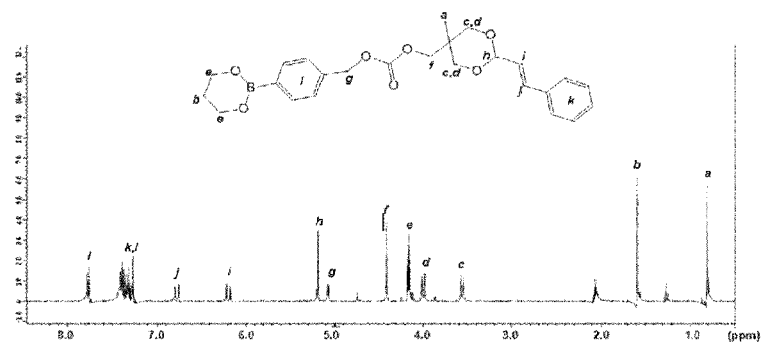

[Fig. 4]
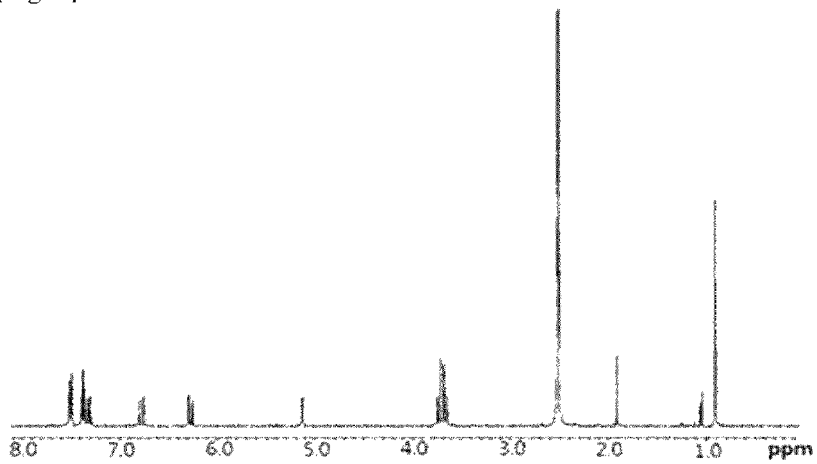
[Fig. 5]
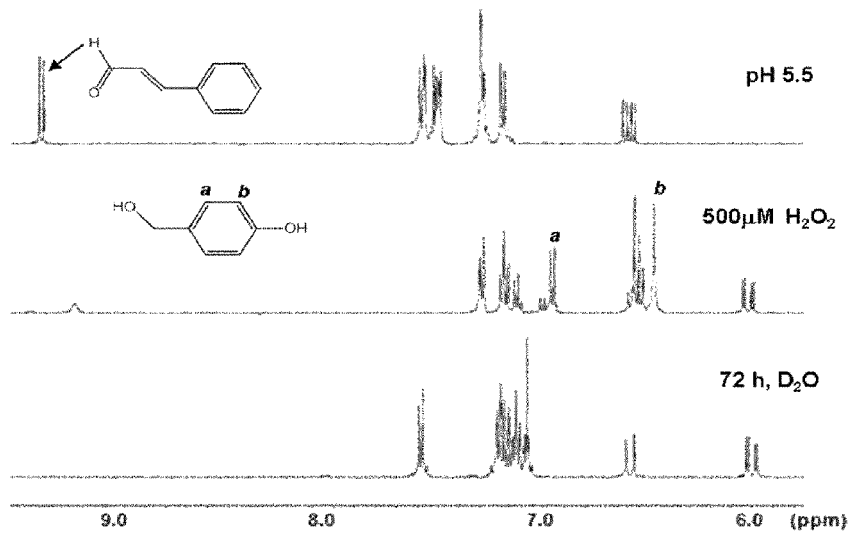
[Fig. 6]
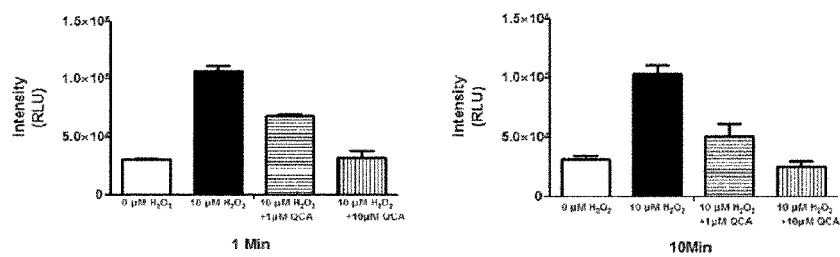

[Fig. 7]
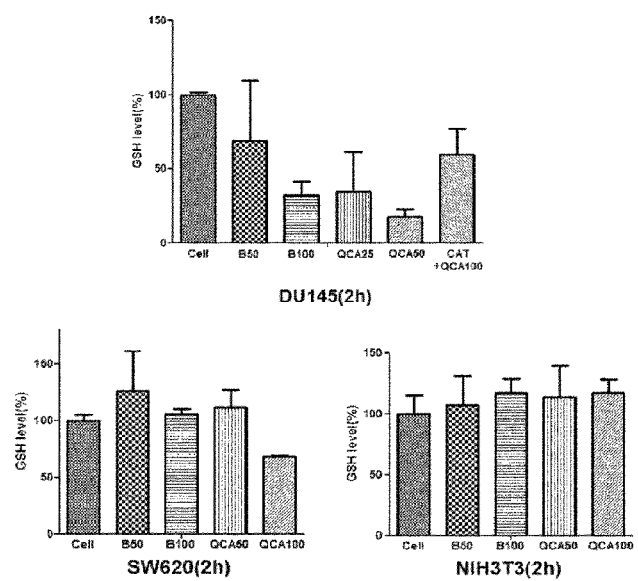
[Fig. 8]
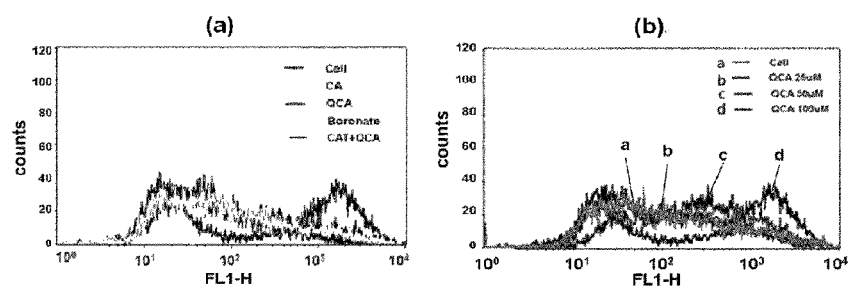

[Fig. 9]
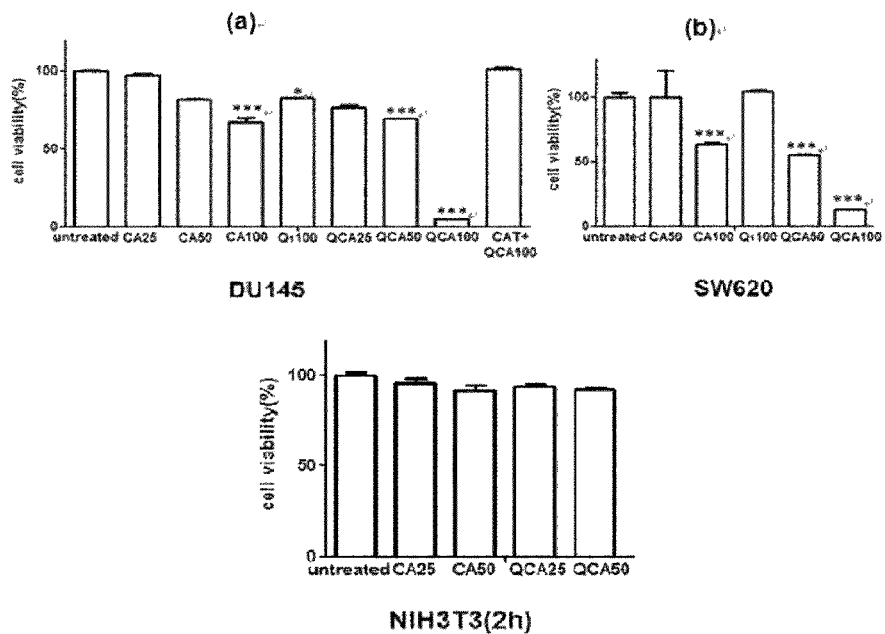
[Fig. 10]
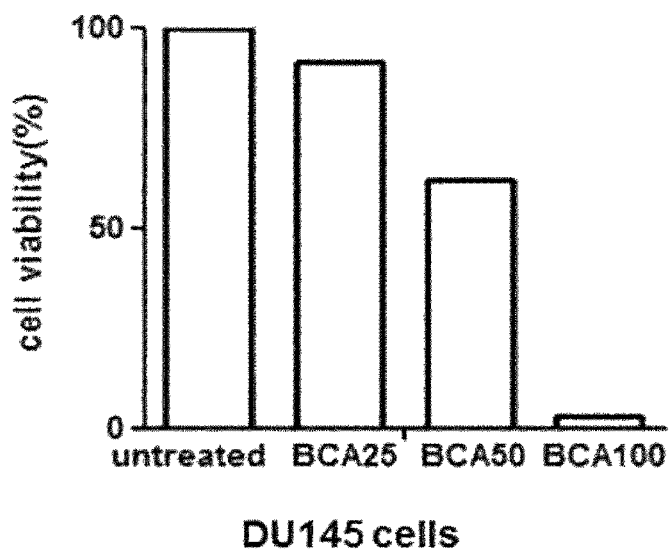

[Fig. 11]
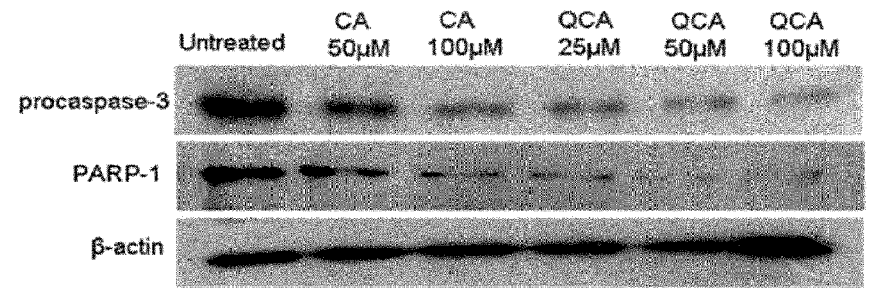
[Fig. 12]
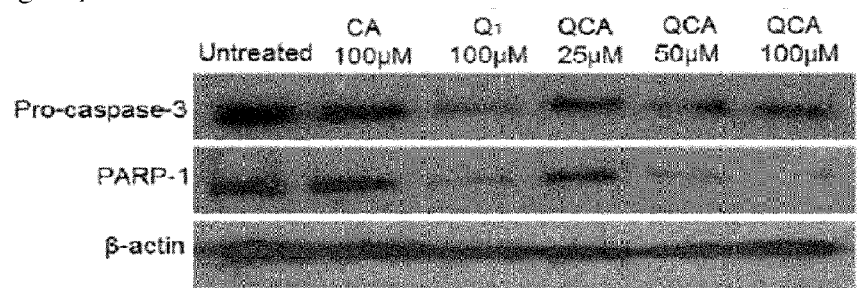
[Fig. 13]
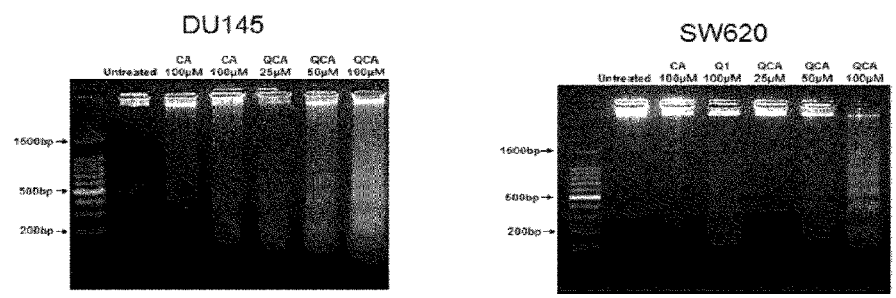
[Fig. 14]
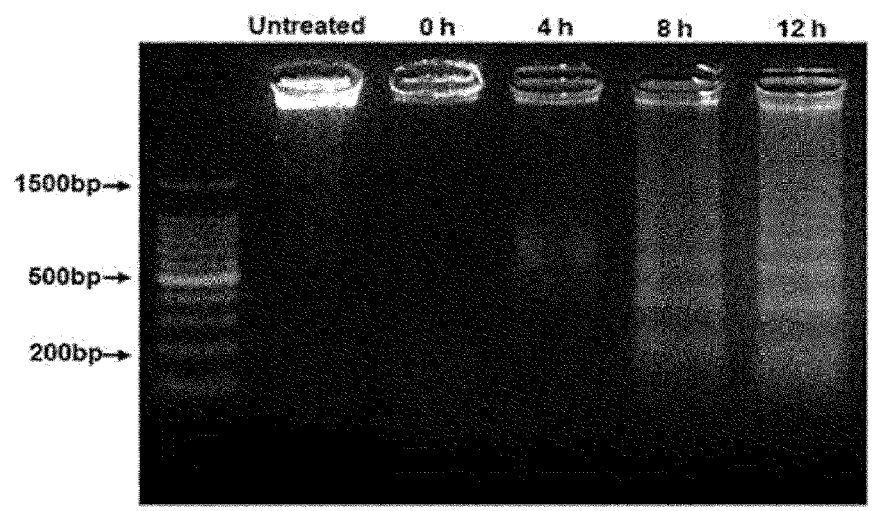

[Fig. 15]
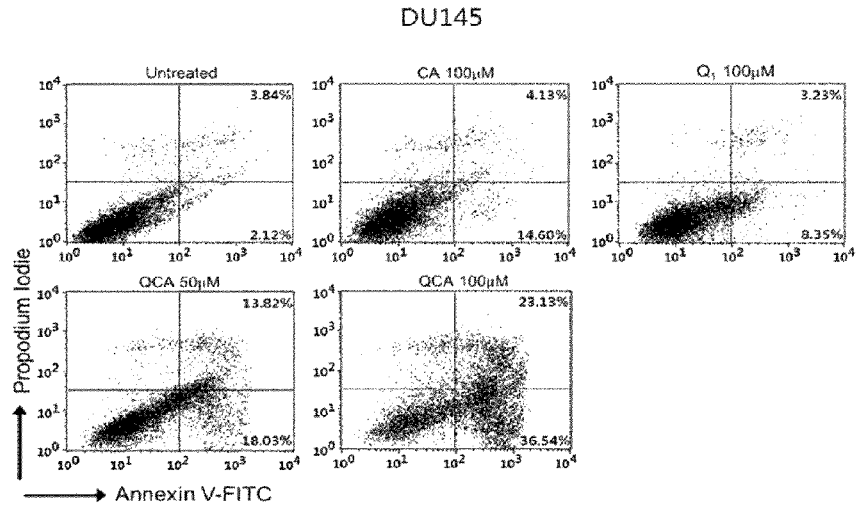
[Fig. 16]
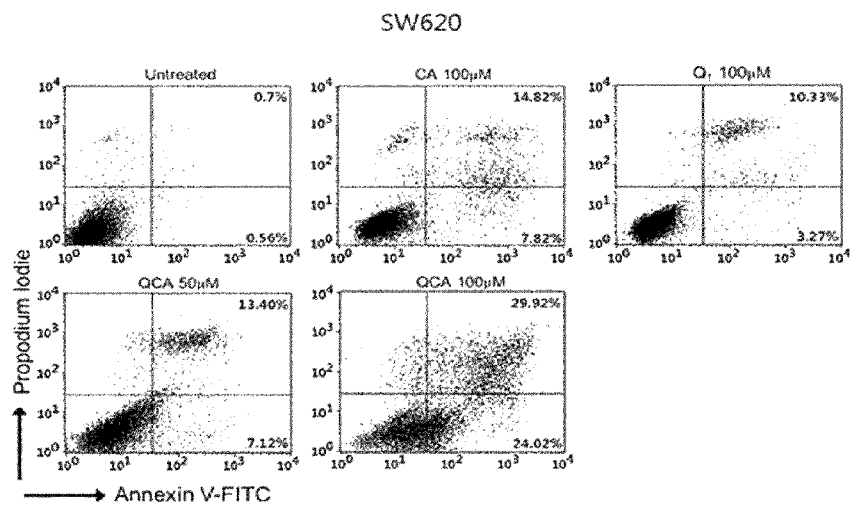
[Fig. 17]
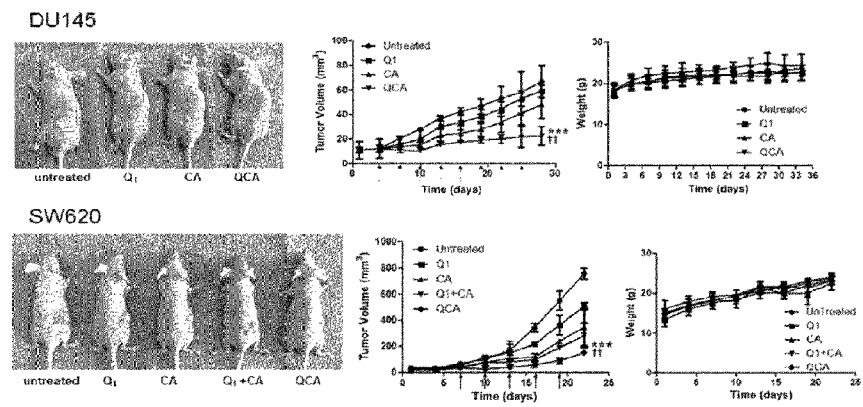

[Fig. 18]
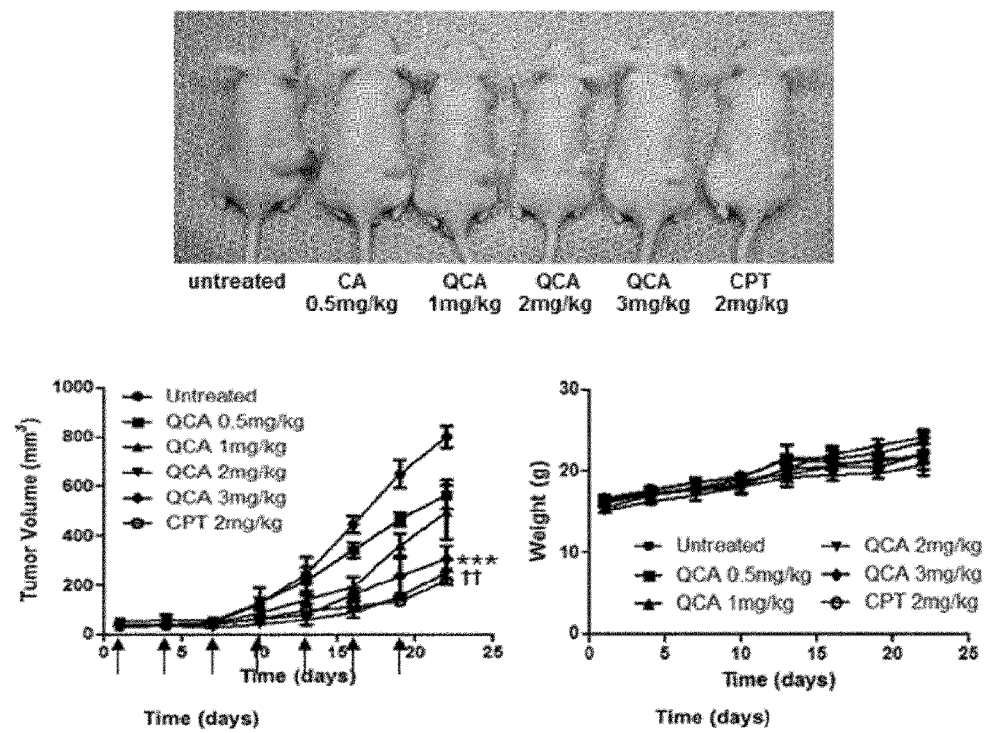

[Fig. 19]
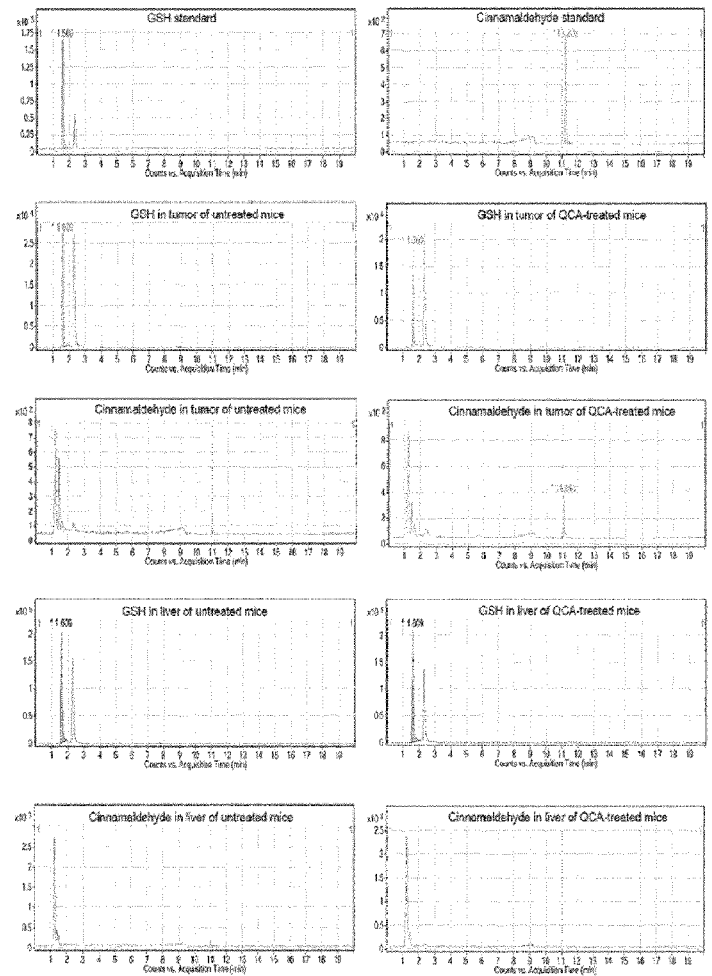
[Fig. 20]
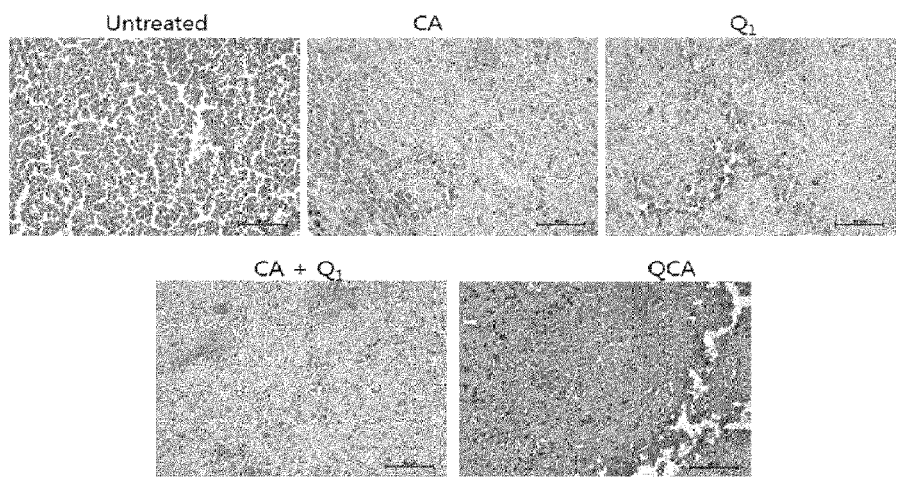

[Fig. 21]
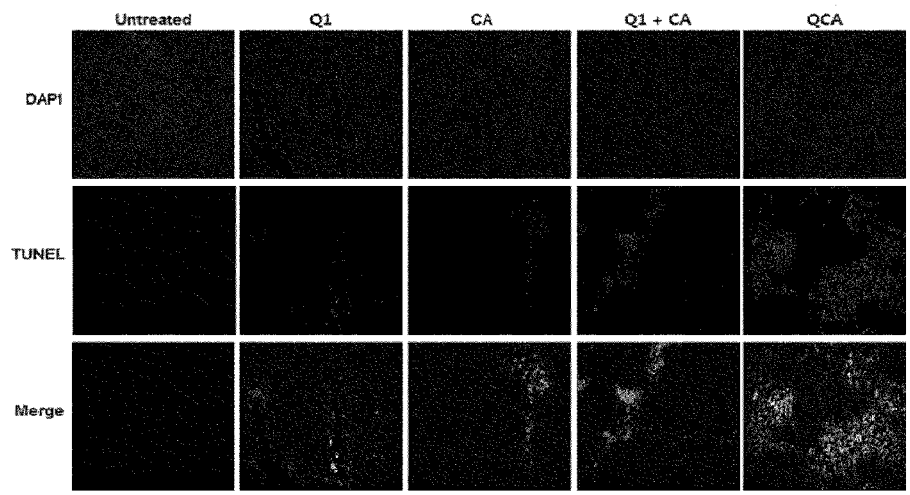
[Fig. 22]
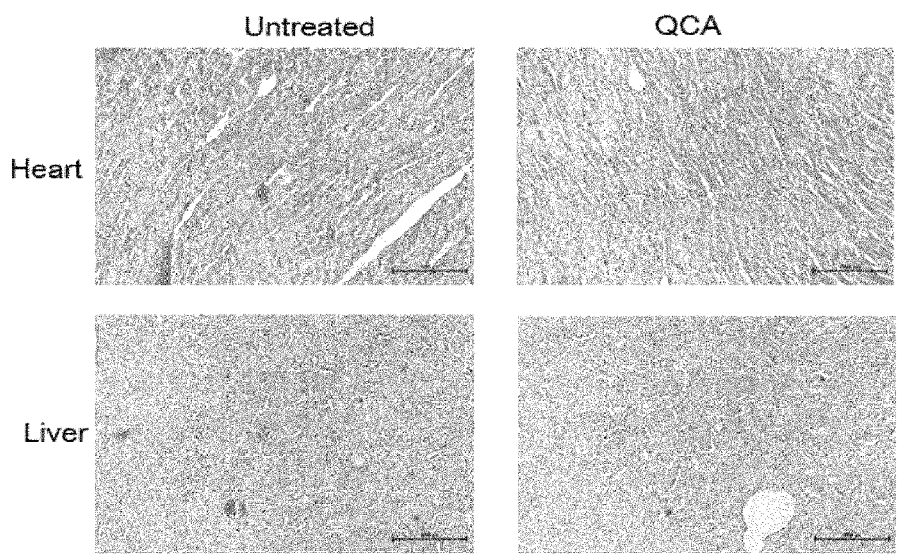
[Fig. 23]
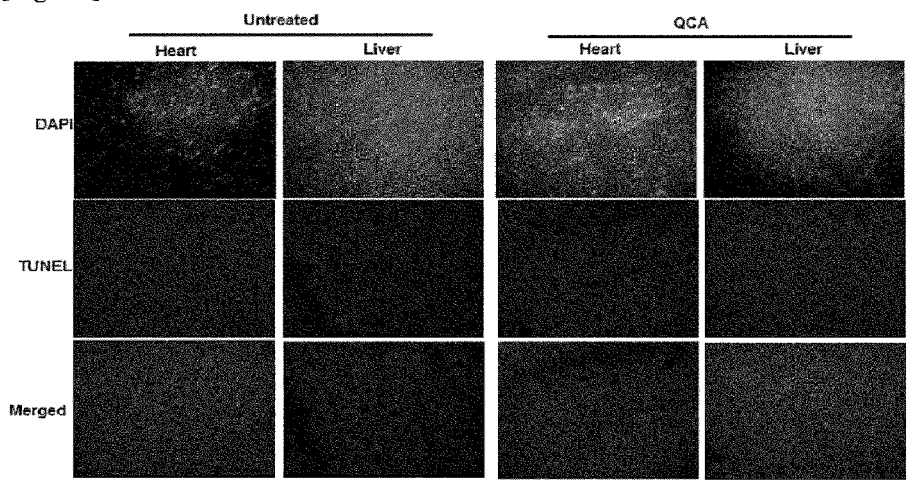

[Fig. 24]
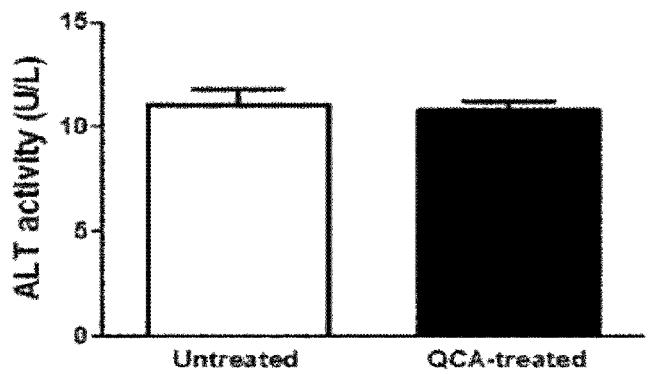
[Fig. 25]
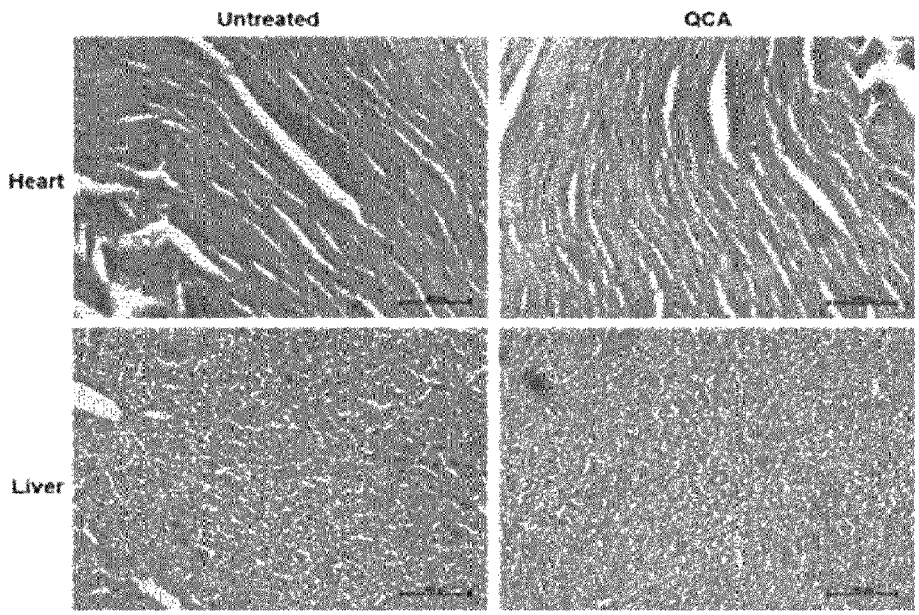

HYBRID ANTICANCER PRODRUG SIMULTANEOUSLY PRODUCING CINNAMALDEHYDE AND QUINONE METHIDE AND METHOD FOR PREPARING SAME

TECHNICAL FIELD

The present invention relates to a hybrid anticancer prodrug simultaneously producing cinnamaldehyde and quinone methide, and more particularly, to a hybrid anticancer prodrug inducing apoptosis of cancer cells while increasing oxidation stress as a complementary synergetic action and a method for preparing the same.

BACKGROUND ART

Cancer is defined that "normal cells which can be regularly proliferated and suppressed in an object if necessary and non-differentiated cells which are unlimitedly proliferated regardless of a required state in a tissue unlike the normal cells are constituted to form a tumor", and the normal cells in the body are changed in genes in the cells due to a specific reason to be modified into cancer cells. All over the world, the cancer occupies approximately 13% of the entire death causes, and is caused without distinction of sex and age and a terrible disease which occupies a second death cause in the worldwide and a first death cause in Korea, and thus researches for targeting conquer cancer have been actively conducted. In the researches, development of efficient anticancer agents which have fewer side effects and can overcome resistance due to diversity of the cancer and diversification of pathogenesis has been required and new anticancer agents are being continuously released.

A stimulus-response system means that a carrier causes changes in phase transition, swelling, degradation, and the like in response to an external environment such as a pH, a temperature, an ionic strength, an electric field, a magnetic field, light, and an ultrasonic wave. The stimulus-response system is mainly used in a release control system induced to protect a drug and adjust a release speed of the drug, or leave the drug in a specific portion. Particularly, the pH of the cancer portion is different from a pH (7.4±0.04) in a general body and various functional groups sensitive to the pH are present and thus, the stimulus-response system has been very widely used.

Meanwhile, cinnamaldehyde is a main component of cinnamon bark as a main active ingredient of cinnamomum cassia in the Lauraceae plant which has been used for treating dyspepsia, gastritis, blood circulation disorders, and inflammation in both East and West. The cinnamaldehyde is a material which includes a α,β-carbonyl group which is known as a Michael receptor pharmacophore, generates reactive oxygen species (ROS) to deteriorate a mitochondrial membrane potential, and thus releases a cytochrome C to a cytosol in the cells to induce apoptosis, and anticancer ability through a mechanism depending on caspase has been proved. However, in spite of excellent anticancer abilities of the cinnamaldehyde and derivatives thereof, phagocytosis is rapidly performed by liver macrophagocytic cells in the body and there is a disadvantage that there is no ability capable of targeting the cancer due to a short half-life of less than 1.5 hr (several minutes and approximately 5 min). Therefore, in order to apply the cinnamaldehyde to an anticancer treatment in clinical, development of physical and chemical modification or new drug delivery systems for enhancing the anticancer effect has been required.

Further, it is known that quinone methide reacts with glutathione (GSH) as a required antioxidant enzyme in the cancer cells to decrease an antioxidative level and thus relatively increases oxidation stress and causes an anticancer effect.

Therefore, the present inventors conducted researches for preparing a hybrid anticancer prodrug which enhances a short retention time which is a disadvantage of cinnamaldehyde inducing apoptosis and a medicinal effect and performs synergetic action to enhance the effect thereof. As a result, the present inventors synthesized 4-(1,3,2-dioxaborinan-2-yl)benzyl ((5-methyl-2-styryl-1,3-dioxan-5-yl)methyl)carbonate (QCA) and 4-(1,3,2-dioxaborinan-2-yl)benzyl ((5-methyl-2-(2-benzoyloxyphenyl)vinyl-1,3-dioxan-5-yl)methyl)carbonate (QBCA) which are prodrugs simultaneously generating cinnamaldehyde and quinone methide, verified a possibility as a new anticancer therapeutic agent of the prepared QCA and QBCA which enhances the retention time of the cinnamaldehyde, minimize side effects by selectively acting in the cancer cells, and maximally have the anticancer effect to complete the present invention.

DISCLOSURE

Technical Problem

The present invention is directed to provide a hybrid anticancer prodrug simultaneously producing cinnamaldehyde and quinone methide, and more particularly, to a hybrid anticancer prodrug inducing apoptosis of cancer cells while increasing oxidation stress as a complementary synergetic action and a method for preparing the same.

Further, the present invention is directed to provide a composition for preventing or treating cancer including the hybrid anticancer prodrug as an active ingredient.

Technical Solution

One aspect of the present invention provides a hybrid anticancer prodrug simultaneously producing cinnamaldehyde and quinone methide, and more particularly, a hybrid anticancer prodrug inducing apoptosis of cancer cells while increasing oxidation stress as a complementary synergetic action and a method for preparing the same.

Further, another aspect of the present invention provides a pharmaceutical composition for preventing or treating cancer including the hybrid anticancer prodrug as an active ingredient.

Further, yet another aspect of the present invention provides a food composition for preventing or improving cancer including the hybrid anticancer prodrug as an active ingredient.

Advantageous Effects

The hybrid anticancer prodrug according to the present invention sequentially releases quinone methide and cinnamaldehyde by $H_2O_2$ and acidic pH, and thus alkylates antioxidant GSH through the release of quinone methide, thereby inhibiting an antioxidative system and increasing oxidation stress, and generates and accumulates reactive oxygen species (ROS) through the release of cinnamaldehyde, thereby promoting apoptosis, and thus the hybrid anticancer prodrug according to the present invention can be favorably used as an anticancer drug by creating a synergetic anticancer effect through double stimulus-response and sequential treatment action in a cancer cell-specific manner.

DESCRIPTION OF DRAWINGS

FIG. 1 is a diagram illustrating a $^1$H-NMR spectrum of 4-(1,3,2-dioxaborinan-2-yl) phenyl) methanol (1) prepared in Example 1-1 of the present invention.

FIG. 2 is a diagram illustrating a $^1$H-NMR spectrum of a cinnamaldehyde derivative (2) prepared in Example 1-2 of the present invention.

FIG. 3 is a diagram illustrating a $^1$H-NMR spectrum of QCA prepared in Example 1-4 of the present invention.

FIG. 4 is a diagram illustrating a $^1$H-NMR spectrum of [4-(1,3,2-dioxaborinan-2-yl)phenyl]methyl N-(5-methyl-2-styryl-1,3-dioxan-5-yl)carbamate prepared in Example 3-4 of the present invention.

FIG. 5 is a diagram illustrating a $^1$H-NMR spectrum after a hydrolysis reaction in cancer cells of the QCA prepared in Example 1-4 of the present invention.

FIG. 6 is a diagram illustrating a result of measuring sensitivity of QCA for $H_2O_2$ by chemiluminescence.

FIG. 7 is a diagram illustrating a result of measuring changes in GSH levels when treating the QCA of the present invention in cells.

FIG. 8 is a diagram illustrating a result of measuring whether to generate reactive oxygen species when treating the QCA of the present invention in cells.

FIG. 9 is a diagram illustrating a result of measuring cytotoxicity when treating the QCA of the present invention in cells.

FIG. 10 is a diagram illustrating a result of measuring cytotoxicity when treating QBCA of the present invention in cells.

FIG. 11 is a diagram illustrating a result of western blot analysis when treating QCA of the present invention in DU145 cells.

FIG. 12 is a diagram illustrating a result of western blot analysis when treating QCA of the present invention in SW620 cells.

FIG. 13 is a diagram illustrating a result of analyzing fragments of DNA in the SW620 cells treated with the QCA of the present invention by electrophoresis.

FIG. 14 is a diagram illustrating a result of analyzing fragments of DNA in the SW620 cells treated with the QCA of the present invention over time.

FIG. 15 is diagram illustrating a flow cytometry result of the DU145 cells treated with the QCA of the present invention.

FIG. 16 is diagram illustrating a flow cytometry result of the SW620 cells treated with the QCA of the present invention.

FIG. 17 is diagram illustrating a result of measuring a size of a tumor in a xenograft model according to administration of the QCA of the present invention.

FIG. 18 is diagram illustrating a result of measuring a size of a tumor in a xenograft model according to a dosage of the QCA of the present invention.

FIG. 19 is diagram illustrating a result of analyzing a tumor lysate in mouse administrated with the QCA of the present invention by LC-MS/MS.

FIG. 20 is a diagram verifying apoptosis of SW620 cells treated with the QCA of the present invention through H&E staining.

FIG. 21 is a diagram verifying apoptosis of SW620 cells treated with the QCA of the present invention through TUNEL staining.

FIG. 22 is a diagram verifying whether organs are damaged through H&E staining of liver and heart tissues in the mouse administrated with the QCA of the present invention.

FIG. 23 is a diagram verifying whether organs are damaged through TUNEL staining of liver and heart tissues in the mouse administrated with the QCA of the present invention.

FIG. 24 is a diagram verifying whether or not toxicity of the QCA through ALT evaluation of in mouse administrated with the QCA of the present invention.

FIG. 25 is a diagram verifying whether or not toxicity of the QCA through H&E staining of liver and heart tissues in mouse administrated with the QCA of the present invention.

MODES OF THE INVENTION

Hereinafter, exemplary embodiments of the present invention will be described in detail. However, the present invention is not limited to the exemplary embodiments disclosed below, but can be implemented in various forms. The following exemplary embodiments are described in order to enable those of ordinary skill in the art to embody and practice the invention.

It will be understood that, although the terms first, second, and the like may be used herein to describe various elements, these elements should not be limited by these terms. These terms are only used to distinguish one element from another. For example, a first element could be termed a second element, and, similarly, a second element could be termed a first element, without departing from the scope of the present invention. As used here, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined here.

The present invention provides a hybrid anticancer prodrug represented by the following Formula 1, as a hybrid anticancer prodrug simultaneously producing cinnamaldehyde and quinone methide.

[Formula 1]

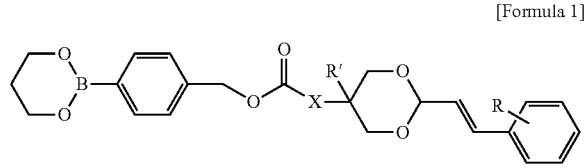

In Formula 1, R is H—, HO—, $CH_3O$—, or $C_6H_5COO$—, R' is H— or $CH_3$—, and X is O or NH.

Hereinafter, the present invention will be described below in more detail.

Generally, the cinnamaldehyde induces apoptosis through generation of reactive oxygen species (ROS), but has a weak cytotoxicity in normal cells. However, application thereof has been limited by a short half-life in the blood of the cinnamaldehyde a lower activity than a general anti-cancer drug. Accordingly, in order to overcome the disadvantage, in the present invention, 4-(1,3,2-dioxaborinan-2-yl)benzyl ((5-methyl-2-styryl-1,3-dioxan-5-yl)methyl)carbonate (QCA), 4-(1,3,2-dioxaborinan-2-yl)benzyl ((5-methyl-2-(2-benzoyloxyphenyl)vinyl-1,3-dioxan-5-yl)methyl)carbonate (QBCA), and [4-(1,3,2-dioxaborinan-2-yl)phenyl]methyl N-(5-methyl-2-styryl-1,3-dioxan-5-yl)carbamate as new hybrid anticancer prodrugs are prepared by binding a quinone methide part removing an antioxidant to the cinnamaldehyde, and represented by the following Formulas 2 to 4.

[Formula 2]

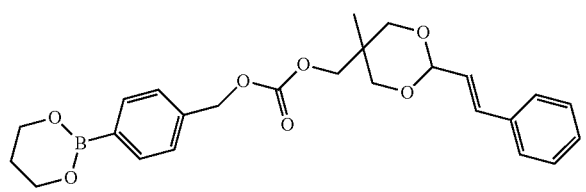 [SMILES: CC1(COC(=O)OCc2ccc(B3OCCCO3)cc2)COC(/C=C/c2ccccc2)OC1]

[Formula 3]

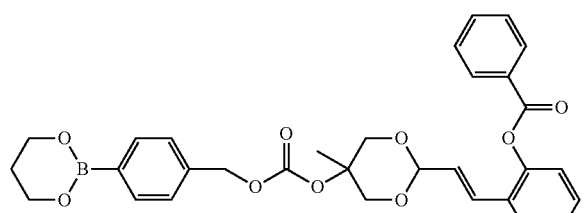

[Formula 4]

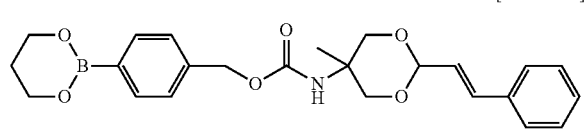

The hybrid anticancer prodrug is constituted by a boronate compound part generating the quinone methide and a cinnamaldehyde derivative, and the boronate compound part and the cinnamaldehyde derivative part may be connected to carbonate (—OCOO—) or carbamate (—NHCOO—). Herein, the boronate compound part needs to be connected with —COO—.

The quinone methide and the cinnamaldehyde may be generated by hydrogen peroxide ($H_2O_2$) and acidic pH, and particularly, may be specifically generated in cancer cells.

In this case, the quinone methide is generated through boronate oxidation by hydrogen peroxide, and in this case, the generated quinone methide alkylates glutathione (GSH) as an antioxidant to inhibit an antioxidative system and increase oxidation stress. Further, the acidic pH cleaves an acetal bond of the present invention to release the cinnamaldehyde, and in this case, the released cinnamaldehyde generates the ROS to promote apoptosis. While the antioxidative level is decreased, a large amount of ROS generated by the release of the cinnamaldehyde is accumulated to further promote the apoptosis. Accordingly, the hybrid anticancer prodrug of the present invention has a synergetic anticancer effect through double stimulus-response and sequential treatment action in a cancer cell-specific manner.

Further, the present invention provides a method for preparing a hybrid anticancer prodrug comprising the steps of:

(a) preparing a boronate compound generating quinone methide by reacting a diol compound and a boronic acid compound;

(b) preparing a cinnamaldehyde derivative having an acetal bond by reacting cinnamaldehyde with an acidic solution;

(c) preparing a cinnamaldehyde release compound by reacting the cinnamaldehyde derivative prepared in step (b) with carbonyldiimidazole; and (d) reacting the cinnamaldehyde release compound prepared in step (c) with the boronate compound prepared in step (a).

A representative example of the method for preparing the hybrid anticancer prodrug of the present invention may be represented by the following Reaction Formula 1.

[Reaction Formula 1]

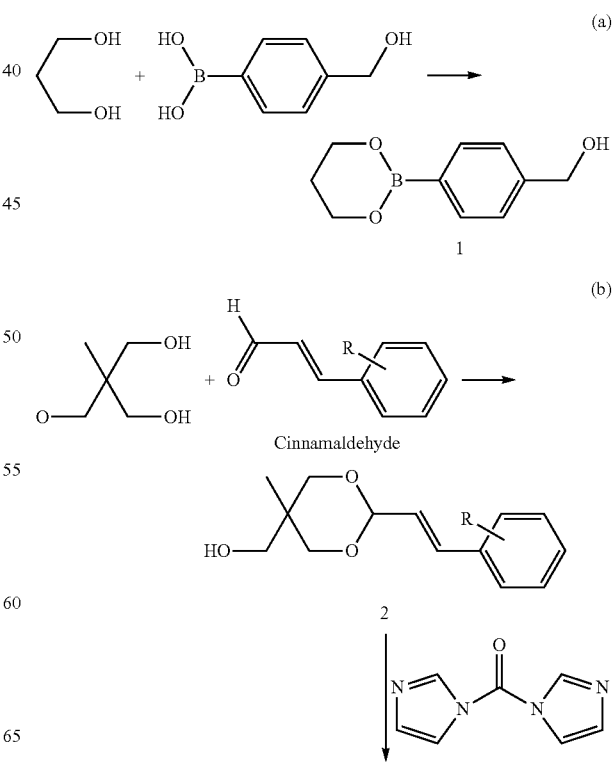

-continued

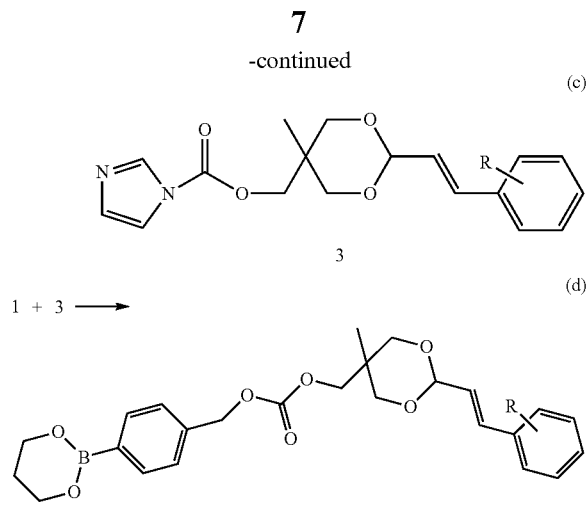

In the Reaction Formula 1, R is defined in Formula 1.

The method for preparing the hybrid anticancer prodrug of the present invention will be described below in detail for each step.

The step (a) is a step of preparing the boronate compound generating the quinone methide and in the step (a), the boronate compound is prepared by reacting the diol compound and the boronic acid compound under an organic solvent.

The diol compound is preferably propanediol, butanediol, or pentanediol, but is not limited thereto, and the boronic acid compound is preferably 4-Hydroxymethylphenyl)boronic acid, 4-(hydroxymethyl)-2-methylphenyl)boronic acid, or 2-fluoro-4-(hydroxymethyl)phenyl)boronic acid.

The step (b) is a step of preparing the cinnamaldehyde derivative having the acetal bond, and in the step (b), the cinnamaldehyde is added in an acidic solution and reacts at a high temperature of 70 to 100° C. and then obtained by evaporating the solvent. The acidic solution is preferably p-toluene sulfonic acid or sulfuric acid, but is not limited thereto.

The prepared cinnamaldehyde derivative can be decomposed in acid by including the acetal bond, thereby releasing the cinnamaldehyde in the cancer cells.

The step (c) is a step of preparing the cinnamaldehyde release compound, and the cinnamaldehyde release compound is obtained by dissolving the cinnamaldehyde derivative prepared in step (b) in an organic solvent together with carbonyl imidazole, reacting at 20 to 40° C., and evaporating the solvent.

The step (d) is a step of preparing the hybrid anticancer prodrug simultaneously generating the cinnamaldehyde and the quinone methide, and the hybrid anticancer prodrug is obtained by reacting the boronate compound prepared in the step (a) and the cinnamaldehyde release compound prepared in the step (c) in an organic solvent and evaporating the solvent.

The organic solvent used in each step may include tetrahydrofuran, dichloromethane, hexane, dioxane, benzene, dimethylsulfoxide, dimethylformamide, and the like, but is not limited thereto.

Further, a method for preparing the hybrid anticancer prodrug of the present invention may include the steps of:
(a) preparing a boronate compound generating quinone methide by reacting a diol compound and a boronic acid compound;
(b) preparing a cinnamaldehyde derivative having an acetal bond by reacting cinnamaldehyde with an acidic solution;
(c) preparing a quinone methide release compound by reacting the boronate compound prepared in the step (a) with the carbonyl imidazole; and
(d) reacting the cinnamaldehyde compound prepared in the step (b) and the quinone methide release compound prepared in the step (c).

A representative example of the preparing method of the present invention may be represented by the following Reaction Formula 2.

[Reaction Formula 2]

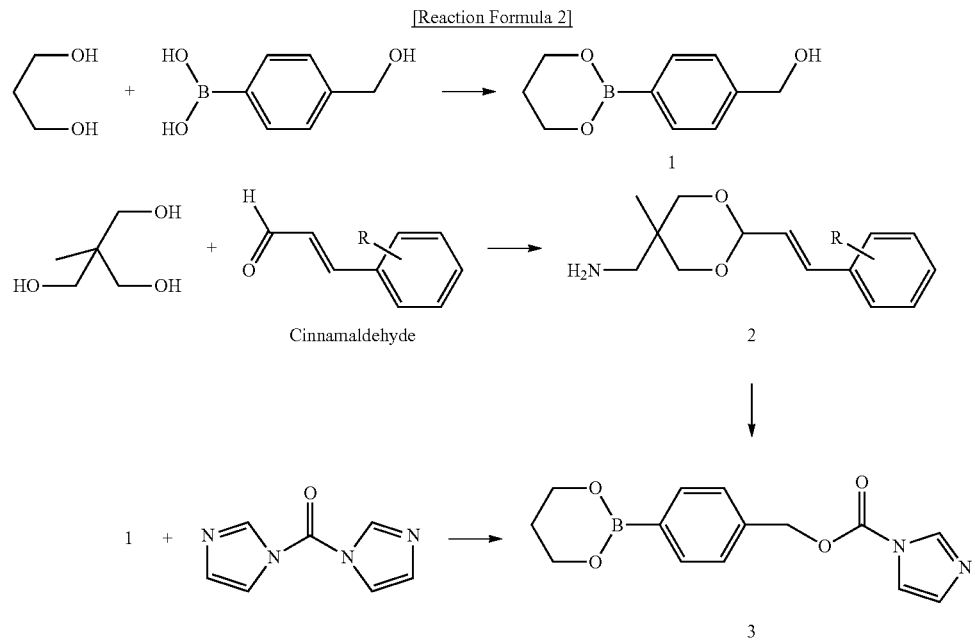

-continued

2 + 3 ⟶ 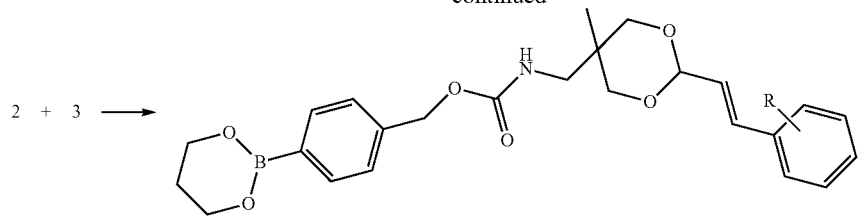

In the Reaction Formula 2, R is defined in Formula 1.

A representative example of a process of decomposing the hybrid anticancer prodrug of the present invention may be represented by the following Reaction Formula 3.

[Reaction Formula 3]

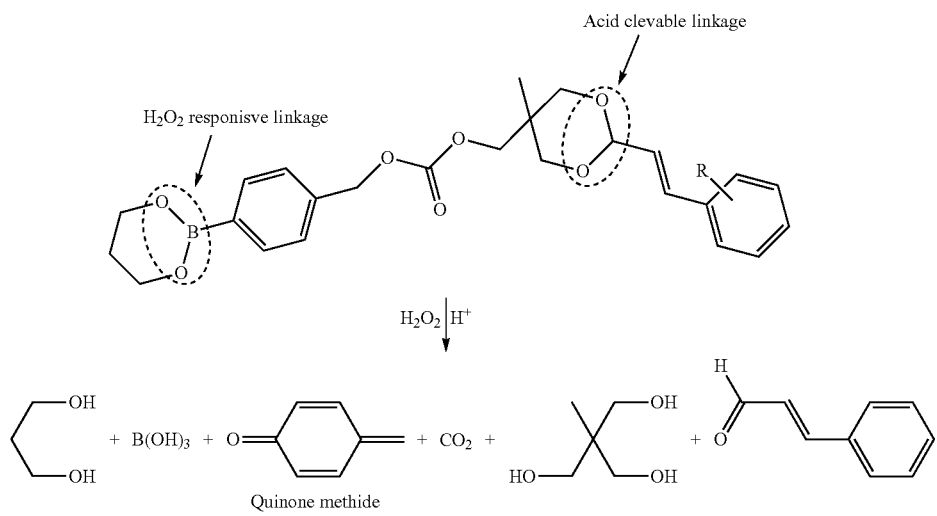

In the Reaction Formula 3, R is defined in Formula 1.

Further, the present invention provides a pharmaceutical composition for preventing or treating cancer including the hybrid anticancer prodrug as an active ingredient.

The composition includes a pharmaceutical composition or a food composition.

The hybrid anticancer prodrug of the present invention sequentially releases the quinone methide and the cinnamaldehyde by $H_2O_2$ and acidic pH, and thus alkylates an antioxidant GSH through the release of the quinone methide, thereby inhibiting an antioxidative system and increasing oxidation stress. Further, while the antioxidative level is decreased, a large amount of reactive oxygen species (ROS) generated by the release of the cinnamaldehyde is accumulated to promote apoptosis, and thus the hybrid anticancer prodrug according to the present invention can be favorably used as an anticancer drug by creating a synergetic anticancer effect through double stimulus-response and sequential treatment action in a cancer cell-specific manner.

The cancer may be any one selected from the group consisting of lung cancer, pancreatic cancer, colon cancer, colorectal cancer, myeloid leukemia, thyroid cancer, myelodysplastic syndromes (MDS), bladder carcinoma, epidermal carcinoma, melanoma, breast cancer, prostate cancer, head and neck cancer, uterine cancer, ovarian cancer, brain cancer, stomach cancer, laryngeal cancer, esophageal cancer, bladder cancer, oral cancer, mesenchymal-origin cancer, sarcomas, teratocarcinomas, neuroblastomas, kidney cancer, liver cancer, non-Hodgkin's lymphomas, multiple myeloma, and anaplastic thyroid carcinoma.

The composition of the present invention may further include one or more kinds of known active ingredients having an effect of preventing or treating the cancer together with the hybrid anticancer prodrug.

The composition of the present invention may further include a carrier, an excipient, and a diluent which are properly and generally used in preparation of the pharmaceutical composition. Further, the composition of the present invention may be formulated and used in forms, such as an oral formulation such as a powder, a granule, a tablet, a capsule, a suspension, an emulsion, syrup, and an aerosol, an external preparation, a suppository, and a sterile injection solution according to a general method. It is preferred that a proper medicine which is known in the art uses a medicine disclosed in the document (Remington's Pharmaceutical Science, recently, Mack Publishing Company, Easton Pa.). The carrier, the excipient, and the diluent which may be included in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like. When the composition is formulated, the formulation may be prepared by using a diluent or an excipient, such as a filler, an extender, a binder, a wetting agent, a disintegrating agent, and a surfactant which are generally used. A solid formulation for oral administration includes a tablet, a pill, a powder, a granule, a capsule, and the like, and the solid formulation may be prepared by mixing at least one excipient, for example, starch, calcium carbonate, sucrose or lactose, gelatin, and the like with the composition. Further, lubricants such as magnesium stearate and talc may be used in addition to simple excipients. A liquid formulation for oral administration may use a suspension, a solution, an emulsion, a syrup, and the like, and may include various excipients, for example, a wetting agent, a sweetener, an aromatic agent, a preserving agent, and the like in addition to water and liquid paraffin as simple diluents which are commonly used. A formulation for parenteral administration includes a sterile aqueous solution, a non-aqueous solution, a suspension, an emulsion, and a lyophilizing agent, and a suppository. As the non-aqueous solution and the suspension, propylene glycol, polyethylene glycol, a vegetable oil such as an olive oil, injectable ester such as ethyl oleate, and the like may be used. As a matter of the suppository, witepsol, macrogol, tween 61, cacao butter, laurin, glycerogelatin, and the like may be used.

The term "administration" used in the present invention means providing a predetermined composition of the present invention to an object by any proper method.

A preferable administration amount of the pharmaceutical composition of the present invention varies according to a state and a weight of the object, the degree of the disease, a drug form, and administration route and period, but may be properly selected by those skilled in the art. For a preferable effect, the hybrid anticancer prodrug of the present invention may be administrated with an amount of 1 mg/kg to 10,000 mg/kg per day and may be administrated once or several times a day.

The pharmaceutical composition of the present invention may be administrated to the object by various routes. All methods of administration may be expected, and for example, may be administered by oral, rectal or intravenous, intramuscular, subcutaneous, intrauterine dura mater, or cerebrovascular injection.

The composition of the present invention may be used alone or in combination with methods using surgery, radiation therapy, hormone therapy, chemotherapy, and biological response modifiers for preventing or treating the cancer.

The food composition of the present invention may add the hybrid anticancer prodrug as it is or may be used together other foods or food ingredients, and may be properly used according to a general method. The mixed amount of the active ingredient may be suitably determined according to the purpose of use (prevention, health, or therapeutic treatment). Generally, in preparation of foods or beverages, the composition of the present invention is added with an amount of 15 wt % or less, preferably, 10 wt % or less with respect to a raw material. However, in the case of long-term administration for health and hygiene or health control, the amount may be the range or less. Since there is no problem in terms of safety, the active ingredient may be used with an amount in the range or more.

The kind of food is not particularly limited thereto. Examples of foods which may be added with the material include meat, sausages, bread, chocolate, candies, snacks, cookies, pizza, Ramen, other noodles, gums, dairy products including ice cream, various soups, beverages, tea, drinks, alcohol drinks, and vitamin complex, and include all health foods in the ordinary acceptation.

The health beverage composition of the present invention may include various flavors, natural carbohydrates, or the like as an additional ingredient like general beverages. The aforementioned natural carbohydrates may use natural sweeteners such as monosaccharides such as glucose and fructose, disaccharides such as maltose and sucrose, dextrin and cyclodextrin, synthetic sweeteners such as saccharin and aspartame, and the like. A ratio of the natural carbohydrate is generally about 0.01 to 10 g and preferably about 0.01 to 0.1 g per 100 ml of the composition of the present invention.

The composition of the present invention may additionally include various nutrients, vitamins, electrolytes, flavoring agents, coloring agents, pectic acid and salt thereof, alginic acid and salt thereof, organic acid, a protective colloidal thickener, a pH adjusting agent, a stabilizer, a preservative, glycerin, alcohol, a carbonic acid agent used in a carbonated drink, or the like, in addition to the ingredients. Besides, the composition of the present invention may include pulps for preparing natural fruit juices, fruit juice beverages, and vegetable beverages. The ingredients may be used independently or in combination. Although the ratio of the additives is not critical, generally, the ratio is selected in a range of 0.01 to 0.1 part by weight per 100 parts by weight of the composition of the present invention.

Hereinafter, preferred embodiments will be proposed in order to help understanding the present invention. However, the exemplary embodiments are just provided to easily understand the present invention and contents of the present invention are not limited to the exemplary embodiments.

Example 1. Preparation of 4-(1,3,2-dioxaborinan-2-yl)benzyl ((5-methyl-2-styryl-1,3-dioxan-5-yl)methyl)carbonate (OCA)

1-1. Preparation of 4-(1,3,2-dioxaborinan-2-yl)phenyl)methanol (1)

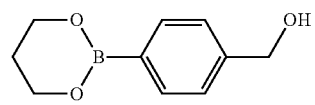

2.0 g of (4-Hydroxymethylphenyl)boronic acid and 1.0 g of 1,3-propanediol were dissolved in 40 mL of dried tetrahydrofuran at room temperature. The reaction mixture was stirred and reacted for 72 hr. The reaction mixture was evaporated under decompression to remove the solvent and purified with a silica-gel chromatography (hexane/ethyl acetate=6/4) to obtain the 4-(1,3,2-dioxaborinan-2-yl)phenyl)methanol compound (1) which was a colorless viscous liquid.

A $^1$H NMR spectrum of the 4-(1,3,2-dioxaborinan-2-yl)phenyl)methanol compound (1) was illustrated in FIG. 1.

1-2. Preparation of Cinnamaldehyde Derivative ((5-methyl-2-styryl-1,3-dioxan-5-yl)methanol) (2)

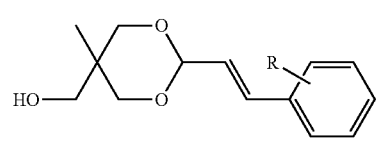

4.88 g of tris(hydroxymethyl)ethane was dissolved in 70 ml of dried benzene. Thereafter, 5.714 mL of cinnamaldehyde and 40 mg of p-toluenesulfonic acid were added to the reaction solution and reacted for 4 hr at 90° C. Thereafter, the reaction solution was cooled at room temperature and added with 1 mL of triethyleneamine to complete the reaction. The benzene in the reaction mixture was evaporated by using a rotary evaporator and the reaction mixture was purified by a column chromatography (hexane/ethyl acetate=7/3) to obtain the cinnamaldehyde derivative compound.

A $^1$H NMR spectrum of the cinnamaldehyde derivative compound was illustrated in FIG. 2.

1-3. Preparation of Cinnamaldehyde Release Compound (3)

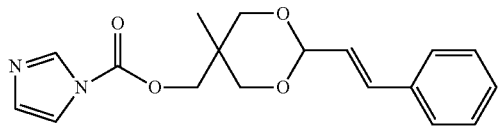

3

4.1 g of 1,1'-Carbonyldiimidazole and 3.0 g of the cinnamaldehyde derivative (2) prepared in Example 1-2 were dissolved in 50 mL of dried dichloromethane to react for 30 min at room temperature. The reaction mixture was evaporated under decompression to remove the dichloromethane and purified by a column chromatography using ethylacetate as a release solvent to obtain the cinnamaldehyde release compound (3).

1-4. Preparation of 4-(1,3,2-dioxaborinan-2-yl)benzyl ((5-methyl-2-styryl-1,3-dioxan-5-yl)methyl)carbonate (QCA)

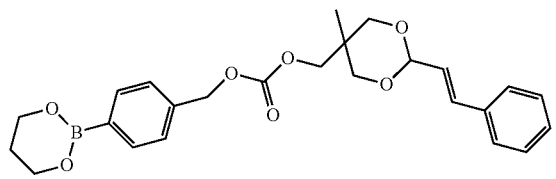

1.0 g of the (4-(1,3,2-dioxaborinan-yl)phenyl)methanol (1) prepared in Example 1-1 and 1.7 g of the cinnamaldehyde release compound (3) prepared in Example 1-3 were dissolved in 50 mL of dried dichloromethane including 0.64 g of 4-(dimethylamino)pyridine and reacted for 24 hr at 40° C. The reaction mixture was evaporated under decompression to remove the solvent and purified with a silica-gel chromatography (hexane/ethyl acetate=5/5) to obtain the QCA compound which was a white solid material.

A $^1$H NMR spectrum of the QCA compound was illustrated in FIG. 3.

As illustrated in FIG. 3, the presence of acetal cations was verified with a peak of 5.1 ppm and a successful binding of the boronate and the cinnamaldehyde was verified with a peak of 4.1 ppm.

Example 2. Preparation of 4-(1,3,2-dioxaborinan-2-yl)benzyl ((5-methyl-2-(2-benzoyloxyphenyl)vinyl-1,3-dioxan-5-yl)methyl)carbonate (QBCA)

2-1. Preparation of 4-(1,3,2-dioxaborinan-2-yl)phenyl)methanol (1)

A compound of 4-(1,3,2-dioxaborinan-2-yl)phenyl)methanol was prepared by the same method as Example 1-1.

2-2. Preparation of Cinnamaldehyde Derivative ((2-(2-(5-hydroxymethyl-5-methyl-1,3-dioxan-2-yl)vinyl)phenyl)benzoate) (2)

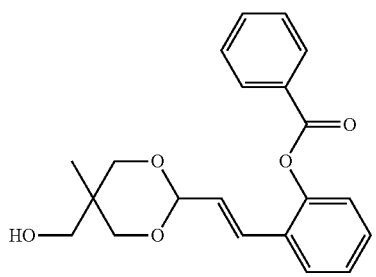

2

Except for using benzoyloxy cinnamaldahyde instead of the cinnamaldehyde in Example 1-2, the cinnamaldehyde derivative compound (2) was prepared by the same method as Example 1-2.

2-3. Preparation of Cinnamaldehyde Release Compound (3)

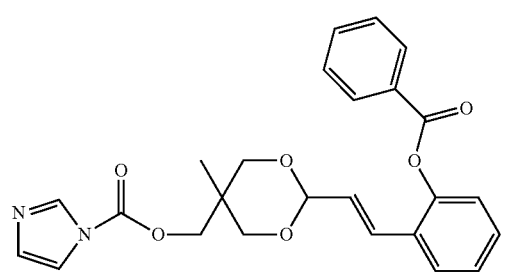

3

Except for using the cinnamaldehyde derivative (2) prepared in Example 2-2 instead of the cinnamaldehyde derivative (2) prepared in Example 1-2 in Example 1-3, the cinnamaldehyde release compound (3) was prepared by the same method as Example 1-3.

2-4. Preparation of 4-(1,3,2-dioxaborinan-2-yl)benzyl ((5-methyl-2-(2-benzoyloxyphenyl)vinyl-1,3-dioxan-5-yl)methyl)carbonate (QBCA)

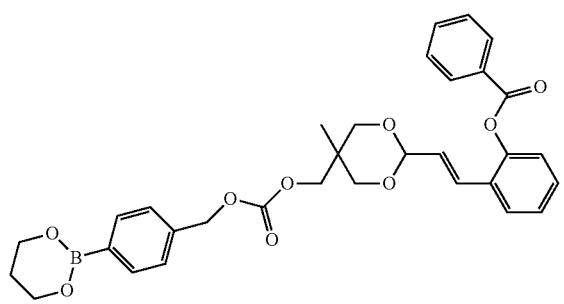 [SMILES: CC1(COC(=O)OCc2ccc(B3OCCCO3)cc2)COC(/C=C/c2ccccc2OC(=O)c2ccccc2)OC1]

Except for using the cinnamaldehyde release compound (3) prepared in Example 2-3 instead of the cinnamaldehyde release compound (3) prepared in Example 1-3 from Example 1-4, the QBCA compound was prepared by the same method as Example 1-4.

Example 3. Preparation of [4-(1,3,2-dioxaborinan-2-yl)phenyl]methyl N-(5-methyl-2-styryl-1,3-dioxan-5-yl)carbamate

3-1. Preparation of (4-(1,3,2-dioxaborinan-2-yl)phenyl)methanol (1)

The 4-(1,3,2-dioxaborinan-2-yl)phenyl)methanol compound was prepared by the same method as Example 1-1.

3-2. Preparation of Cinnamaldehyde Derivative (5-methyl-2-styryl-1,3-dioxan-5-amine) (2)

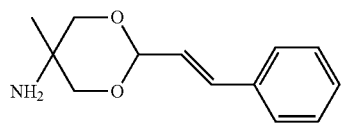

4 g of 2-amino-2-methylpropane-1,3-diol was purified by a column chromatography using ethyl 2,2,2-trifluoroacetate. Herein, 2.63 g of cinnamaldehyde and 5.4 g of ethyl 2,2,2-trifluoroacetate were dissolved in MeOH and reacted for 12 hour at room temperature to obtain N-(1,3-dihydroxy-2-methylpropan-2-yl)-2,2,2-trifluoroacetamide. The obtained N-(1,3-dihydroxy-2-methylpropan-2-yl)-2,2,2-trifluoroacetamide 4 g was added with ethylacetate and reacted for 6 hr at 70° C. in THF to obtain 2,2,2-trifluoro-N-(5-methyl-2-styryl-1,3-dioxan-5-yl)acetamide and the obtained 2,2,2-trifluoro-N-(5-methyl-2-styryl-1,3-dioxan-5-yl)acetamide was purified by a column chromatography (hexane/ethyl acetate=8/2). 2 g of the purified 2,2,2-trifluoro-N-(5-methyl-2-styryl-1,3-dioxan-5-yl)acetamide was dissolved in MeOH and added with 1.2 g potassium carbonate dissolved in water to obtain the cinnamaldehyde derivative (5-methyl-2-styryl-1,3-dioxan-5-amine) (2) for 5 hr at 60° C.

3-3. Preparation of Quinone Methide Release Compound (3)

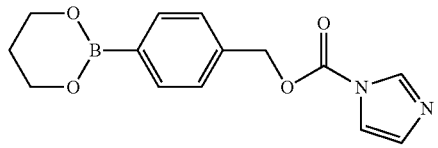

4.1 g of 1,1'-Carbonyldiimidazole and 3.0 g of the boronate compound (1) prepared in Example 3-1 were dissolved in 50 mL of dried dichloromethane and then reacted for 30 min at room temperature. The reaction mixture was evaporated under decompression to remove the dichloromethane and purified by a column chromatography using ethylacetate as a release solvent to obtain the quinone methide release compound (3).

3-4. Preparation of 4-(1,3,2-dioxaborinan-2-yl)phenyl]methyl N-(5-methyl-2-styryl-1,3-dioxan-5-yl)carbamate

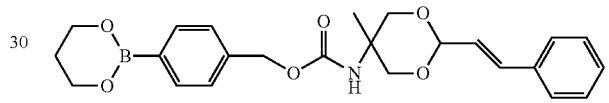

1.0 g of 5-methyl-2-styryl-1,3-dioxan-5-amine (2) prepared in Example 3-2 and 1.7 g of the quinone methide release compound (3) prepared in Example 3-3 were dissolved in 50 mL dried dichloromethane including 0.64 g of 4-(dimethylamino)pyridine and reacted for 24 hr at 40° C. The reaction mixture was evaporated under decompression to remove the solvent and purified with a column chromatography (hexane/ethyl acetate=5/5) to obtain the 4-(1,3,2-dioxaborinan-2-yl)phenyl]methyl N-(5-methyl-2-styryl-1,3-dioxan-5-yl)carbamate compound.

A $^1$H NMR spectrum of the prepared 4-(1,3,2-dioxaborinan-2-yl)phenyl]methyl N-(5-methyl-2-styryl-1,3-dioxan-5-yl)carbamate compound was illustrated in FIG. 4.

As illustrated in FIG. 4, a successful binding of the boronate and the cinnamaldehyde was verified with a peak of 4.1 ppm.

Experimental Example 1. Verification of OCA Structure after Hydrolysis in Tumor Environment In a tumor environment, in order to verify a structure of the QCA triggered by double stimulus, the QCA was cultured for 24 hr at pH 5.5 and verified through $^1$H NMR and the structure of the QCA was illustrated in FIG. 5.

As illustrated in FIG. 5, cinnamaldehyde generated while an acetal bond was broken by a peak of an acetal cation and an aldehyde cation of 9.4 ppm was verified and formation of hydroxybenzyl alcohol and oxidation of $H_2O_2$-mediated boronate were verified by an aromatic cation peak of 6.9 and 6.4 ppm.

However, the cinnamaldehyde was cultured for 72 hr at neutral pH without $H_2O_2$ and then any change was not observed. It was shown that the QCA was activated by $H_2O_2$ and acidic pH in order to generate quinone methide (QM) and bioactive cinnamaldehyde, respectively.

Experimental Example 2. Verification of Sensitivity of OCA to Hydrogen Peroxide

In order to verify sensitivity of the QCA to $H_2O_2$, the QCA reacted in a diphenyl oxalate solution including rubrene and then evaluated by measuring a chemiluminescence intensity. In detail, the QCA was added in 1 μM of a $H_2O_2$ solution and reacted for 1 min. Next, a diphenyl oxalate solution was added in the $H_2O_2$ solution and the chemiluminescence intensity was measured by using a luminometer (Femtomaster FB 12, Zylux Corporation, TN, US). The results were illustrated in FIG. 6.

As illustrated in FIG. 6, an untreated $H_2O_2$ solution had a significantly high chemiluminescence intensity ($1.1 \times 10^5$ RLU), but in the case of adding the QCA, it was verified that the chemiluminescence intensity was significantly reduced concentration-dependently. It was shown that boronate ester rapidly reacts with $H_2O_2$ in the QCA and thus the QCA is activated to release the QM.

Experimental Example 3. Measurement OF Cell GSH Level

A prostate cancer cell line DU145, a colorectal cancer cell line SW620, and a fibroblast cell NIH3T3 were inoculated in a 6-well plate ($5 \times 10^5$/well) to reach 80% confluency. The cell lines were treated with various compounds for 1.5 hr at 37° C. and then, cells were obtained and washed with PBS. Thereafter, the cells were lysed in ice in 40 μL of a Triton X-100 lysis buffer solution. After 20 min, the lysate was centrifuged with 9,000 g and 10 μL of a supernatant was mixed with 50 μL of an Ellman's reagent (0.5 mM DTNB). The amount of GSH was quantified by measuring an absorbance at 405 nm using a microplate reader (Biotek Instruments, Winooski, Vt.). In the treated cells, a percentage of the GSH content was compared with the base GSH content measured in untreated cells, and the result was illustrated in FIG. 7.

As illustrated in FIG. 7, it was verified that the GSH level was significantly reduced in a dose-dependent manner in both the prostate cancer cell line DU145 and the colorectal cancer cell line SW620 in the case of treating the QCA. Most of GSH was depleted during 50 μM administration and the reduction of the GSH during 100 μM administration was not further observed. The QCA further reduces the GSH level in the prostate cancer cell line DU145 than the colorectal cancer cell line SW620, but in the non-malignant fibroblast cell NIH3T3, the QCA has no effect on the GSH level. It was shown that the QM released from the QCA reduced the GSH level in the cancer cells.

Experimental Example 4. Evaluation of Generation Ability of Reactive Oxygen Species Using Flow Cytometry The prostate cancer cell line DU145 ($4 \times 10^5$) was inoculated in a 24-well culture plate and cultured for 24 hr, and treated with cinnamaldehyde or QCA for 12 hr. Cells were washed with a new medium twice and resuspended in a 1× binding buffer at a concentration of $1 \times 10^5$ cells/mL. 100 μL of the cell suspension was transferred to 5 mL of a culture tube and added with 5 μM of 2',7'-dichlorofluorescein diacetate (DCFH-DA) and softly mixed. The cells were dark-cultured for 15 min at room temperature and added with 400 μL of the 1× binding buffer. The stained cells were measured by using a flow cytometry (FACS Caliber, Becton Dickinson, San Jose, Calif.) and the result was illustrated in FIG. 8. A total of $1.5 \times 10^4$ cells per sample were analyzed.

As illustrated in FIG. 8, it was verified that when administrating the hybrid anticancer prodrug QCA of the present invention, apoptosis was shown and much higher cell toxicity than the cinnamaldehyde was shown. It was shown that the reduction of the GSH by the QM made the cells more sensitive to oxidation stress and induced apoptosis of the cancer cells by generating the ROS.

Experimental Example 5. Measurement of Cytotoxity of OCA and QBCA

The cytotoxities of the QCA prepared in Example 1 and the QBCA prepared in Example 2 were measured by an MTT assay. In detail, a prostate cancer cell line DU145, a colorectal cancer cell line SW620, and a fibroblast cell NIH3T3 were inoculated in a 24-well plate with the density of $1 \times 10^5$ cells/well, respectively, and cultured for 24 hr to reach up to 90% confluency. The cells were treated with various amounts of QCA, QBCA, Q1, or cinnamaldehyde and cultured for 24 hr. 100 μL of the MTT solution was put each well and the cells were cultured for 4 hr. The generated formazan crystals were dissolved in 200 μL of dimethylsulfoxide. After 10 min of the culture, an absorbance at 570 nm was measured by using a micro plate reader (Biotek Instruments, Winooski, Vt.). A cell survival rate was determined by comparing absorbances of cells in a control group and QCA or QBCA-treated cells, and the results were illustrated in FIGS. 9 and 10.

As illustrated in FIG. 9, it was verified that the cytotoxicity was increased according to a concentration during the QCA treatment. It was shown that the apoptosis by the generation of the reactive oxygen species was induced.

As illustrated in FIG. 10, it was verified that the cytotoxicity was increased according to a concentration during the QBCA treatment. It was shown that the apoptosis by the generation of the reactive oxygen species was induced.

Experimental Example 6. Immunoblot Analysis

The prostate cancer cell line DU145 and the colorectal cancer cell line SW620 ($1 \times 10^6$/well) were treated with cinnamaldehyde or QCA for 8 hr at various concentrations and washed with new PBS twice. Proteins were extracted from the cells by using a lysis buffer solution. Electrophoresis was performed by using 20 g of a cell lysate in a 1% polyacrylamide gel and the proteins were transferred to a PVDF membrane (Millipore, Billerica, Mass.). A blot was cultured together with a PARP monoclonal antibody (Santa Cruz Biotechnology, Dallas, Tex.) or caspase-3 (Santa Cruz Biotechnology, Dallas, Tex.) and a HRP-coupled anti-goat antibody (Millipore, Billerica, Mass.) was used as a secondary antibody. An immunoblot signal was verified by using a chemiluminescent reagent (Pierce, Rockford, Ill.) of SuperSignal Ultra and the result thereof was illustrated in FIGS. 11 and 12.

As illustrated in FIGS. 11 and 12, it was verified that the QCA which was the hybrid anticancer prodrug of the present invention concentration-dependently reduced expression of procaspase-3 and PARP-1.

Experimental Example 7. Verification of DNA Fragments by ROS

In order to verify an effect of the QCA on the DNA fragments, a DNA fragmentation assay of SW620 was performed. First, the DU145 and SW620 cells were cultured for 24 hr and then treated with 100 μm of cinnamaldehyde, 100 μm of Q1 (4-(1,3,2-dioxaborinan-2-yl)benzyl carbonate, and generating only quinone methide), and 25 μm, 50 μm, 100 μm of the QCA to isolate the DNA and the fragmentation of the nucleosomal DNA was observed by electrophoresis, and the result thereof was illustrated in FIG. 13.

As illustrated in FIG. 13, a typical ladder pattern of apoptosis was shown in the cell treated with the QCA, and it was shown that the QCA induced more DNA fragments than the cinnamaldehyde and the Q1.

Further, hereinabove, the DNA fragments of the SW620 treated with 100 μm of the QCA were analyzed over time and the result thereof was illustrated in FIG. 14.

As illustrated in FIG. 14, the amount of the DNA fragments was gradually increased in a concentration and time-dependent manner, and it was shown that the QCA induced the apoptosis.

Further, in order to support the result of the DNA fragmentation assay, the DU145 and SW620 cells were cultured for 24 hr and treated with cinnamaldehyde, Q1 or QCA for 24 hr and then flow cytometry was performed by using Annexin V-FITC as a marker of apoptosis and propidium iodide (PI) as a marker for cell survival, and the result was illustrated in FIGS. 15 and 16.

As illustrated in FIGS. 15 and 16, it was verified that the QCA-treated cells had faster apoptosis than the cinnamaldehyde and Q1-treated cells and as the dosage of the QCA was increased, Annexin V and PI cells were increased.

Experimental Example 8. Measurement of Growth and Size of Tumor in Xenograft Model In order to verify in vivo anticancer activity of the QCA, a tumor in a xenograft model was observed. First, cancer cells were injected to a side hypodermic tissue of mouse by using a xenograft mouse model of DU145 and SW620 and when the tumor after cell transplantation started to be touched small, cinnamaldehyde, Q1, and cinnamaldehyde and Q1, or QCA was administrated by 2 mg/kg though tail vein every 3 days, and then the size of the tumor in the mouse was measured and the result thereof was illustrated in FIG. 17.

As illustrated in FIG. 17, when only the cinnamaldehyde or only the Q1 was treated, the growth inhibition effect of the tumor was slight and even in the case of administrating the cinnamaldehyde and the Q1 together, the anticancer effect was not large. However, in the case of the QCA-treated mouse, a significantly smaller size of the tumor was verified than the case of administrating the cinnamaldehyde, and Q1, or both the cinnamaldehyde and the Q1. In this case, in the case of the QCA-treated mouse, it was shown that the QCA continuously released the QM and the cinnamaldehyde.

Further, different amounts of QCA were administrated to the mouse having the tumor and in order to compare the effect thereof, 2 mg/kg of camptotethin (CPT) as an anticancer agent which was commercialized was administrated in other mouse, and then the size of the tumor of the mouse was measured and the result thereof was illustrated in FIG. 18.

As illustrated in FIG. 18, in the case of administrating the QCA with 1 mg/kg or less, a different anticancer activity was not shown, but in the case of administrating 2 mg/kg of the QCA, the prominent anticancer activity was shown as compared with the CPT.

Experimental Example 9. Verification of Generation of QM and Cinnamaldehyde

In the tumor, in order to verify whether to generate the QM and the cinnamaldehyde in the tumor, a tumor lysate was analyzed by LC-MS after 22 days and the result thereof was illustrated in FIG. 19.

As illustrated in FIG. 19, it was verified that the tumor of the QCA-treated mouse had the GSH value lower up to 38% than the tumor of the untreated mouse, and it was verified that the cinnamaldehyde was generated due to a presence of the same new peak as the case of treating the cinnamaldehyde. However, the QM and the cinnamaldehyde were not detected in the liver. It was shown that the QCA generated the QM and the cinnamaldehyde in the tumor and oxidation stress inducing the apoptosis of the cancer cells was increased.

Experimental Example 10. Histologic Examination of Tumor

In order to verify the apoptosis induced by the QCA, in a SW620 tumor mouse model, H&E staining of the tumor was performed after administrating cinnamaldehyde, Q1, the cinnamaldehyde and the Q1, or QCA for 21 days once per three days, and the result thereof was illustrated in FIG. 20.

Further, terminal deoxynucleotidyl transferase dUTP nick end labeling (TUNEL) staining of the tumor was performed by the same method, and the result thereof was illustrated in FIG. 21.

As illustrated in FIGS. 20 and 21, unlike a tumor tissue of mouse in a control group without a distinct damage, it was verified that in the tumor of the QCA-treated mouse, apoptosis of no-nuclear cells was widely shown.

Further, in order to verify whether the QCA treatment caused the organ damage, H&E staining and TUNEL staining of liver and heart tissues of the mouse treated by the same method were performed and the result thereof was illustrated in FIGS. 22 and 23.

As illustrated in FIGS. 22 and 23, it was verified that the QCA treatment did not induce a particular organ damage.

Experimental Example 11. Verification of Stability of OCA

In order to verify the stability of the QCA, after 2 mg/kg of the QCA was injected to the mouse for 10 days once per 2 days, alanine transaminase (ALT) evaluation and H&E staining of the liver and heart tissues were performed, and the result thereof was illustrated in FIGS. 24 and 25.

As illustrated in FIGS. 24 and 25, the QCA-treated mouse had a little difference in serum ALT level as compared with the untreated mouse, and the evidence of the toxicity accumulated in the liver and the heart was not observed. It was shown that there was no toxicity of the QCA or much low toxicity of the QCA.

Preparation Examples for the composition of the present invention will be exemplified below.

Preparation Example 1

Preparation of Pharmaceutical Preparations

1. Preparation of Powder

| | |
|---|---|
| Compound of Formula 1 | 20 mg |
| Lactose | 100 mg |
| Talc | 10 mg |

The ingredients were mixed and packed in an airtight bag to prepare the powder.

2. Preparation of Tablet

| | |
|---|---|
| Compound of Formula 1 | 10 mg |
| Corn starch | 100 mg |
| Lactose | 100 mg |
| Magnesium stearate | 2 mg |

The ingredients were mixed and tableted according to a general tablet preparing method to prepare the tablet.

3. Preparation of Capsule

| | |
|---|---|
| Compound of Formula 1 | 10 mg |
| Crystalline cellulose | 3 mg |
| Lactose | 14.8 mg |
| Magnesium stearate | 0.2 mg |

The ingredients were mixed and filled in a gelatin capsule according to a general capsule preparing method to prepare the capsule.

4. Preparation of Injection

| | |
|---|---|
| Compound of Formula 1 | 10 mg |
| Mannitol | 180 mg |
| Sterile distilled water for injection | 2974 mg |
| Na$_2$HPO$_4$2H$_2$O | 26 mg |

The injection was prepared with the content of ingredients per 1 ampoule (2 ml) according to a general method of preparing the injection.

5. Preparation of Solution

| | |
|---|---|
| Compound of Formula 1 | 20 mg |
| Isomerized glucose | 10 g |
| Mannitol | 5 g |
| Purified water | suitable amount |

According to a general preparing method of the solution, respective ingredients were added in purified water and dissolved, added with a suitable amount of lemon flavoring, and mixed and then added with purified water so as to be adjusted to the entire 100 ml, and then filled in a dark amber bottle and sterilized to prepare the solution.

Preparation Example 2

Preparation of Food Composition 2-1. Preparation of Health Food

| | |
|---|---|
| Compound of Formula 1 | 100 mg |
| Vitamin mixture | suitable amount |
| Vitamin A acetate | 70 g |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 g |
| Vitamin C | 10 mg |
| Biotin | 10 g |
| Nicotinic acid amide | 1.7 mg |
| Folic acid | 50 g |
| Calcium pantothenate | 0.5 mg |
| Mineral mixture | suitable amount |
| Ferrous sulfate | 1.75 mg |
| Zinc oxide | 0.82 mg |
| Magnesium carbonate | 25.3 mg |
| First potassium phosphate | 15 mg |
| Second calcium phosphate | 55 mg |
| Potassium citrate | 90 mg |
| Calcium carbonate | 100 mg |
| Magnesium chloride | 24.8 mg |

A composition ratio of the mixture of vitamins and mineral was set by mixing ingredients relatively suitable for a health food, but a mixed ratio may be randomly modified. According to a general method of preparing the health food, the ingredients were mixed to prepare granules and may be used for preparing the health food composition according to a general method.

The invention claimed is:

1. A compound of Formula 1:

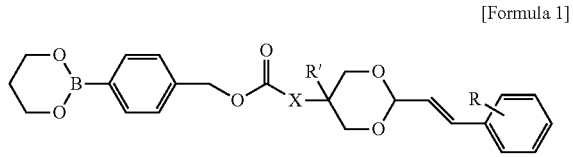

[Formula 1]

wherein

R is H—, HO—, CH$_3$O—, or C$_6$H$_5$COO—;

R' is H— or CH$_3$—, and

X is O, OCH$_2$, or NH.

2. A compound selected from the group consisting of:

4-(1,3,2-dioxaborinan-2-yl)benzyl((5-methyl-2-styryl-1,3-dioxan-5-yl)methyl)carbonate

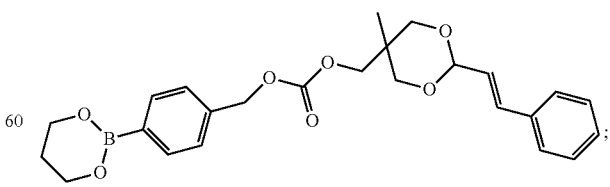

4-(1,3,2-dioxaborinan-2-yl)benzyl((5-methyl-2-(2-benzoyloxyphenyl)vinyl-1,3-dioxan-5-yl)methyl)carbonate

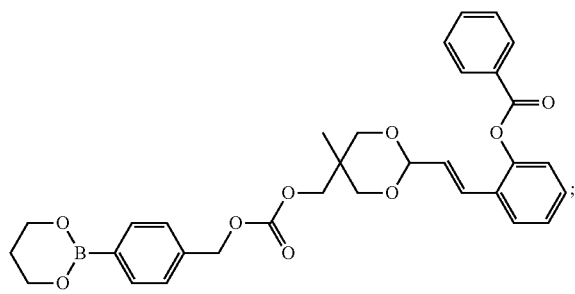 [SMILES: CC1(COC(=O)OCc2ccc(B3OCCCO3)cc2)COC(/C=C/c2ccccc2OC(=O)c2ccccc2)OC1]

and 4-(1,3,2-dioxaborinan-2-yl)phenylmethyl-N-(5-methyl-2-styryl-1,3-dioxan-5-yl)carbamate

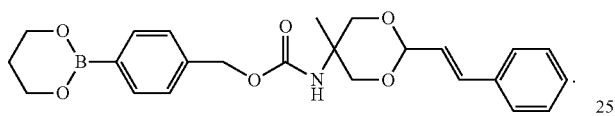

3. The compound of claim 2, wherein the compound is 4-(1,3,2-dioxaborinan-2-yl)benzyl((5-methyl-2-styryl-1,3-dioxan-5-yl)methyl)carbonate:

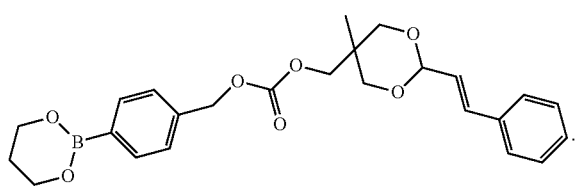 [SMILES: CC1(COC(=O)OCc2ccc(B3OCCCO3)cc2)COC(/C=C/c2ccccc2)OC1]

4. The compound of claim 2, wherein the compound is 4-(1,3,2-dioxaborinan-2-yl)benzyl((5-methyl-2-(2-benzoyloxyphenyl)vinyl-1,3-dioxan-5-yl)methyl)carbonate:

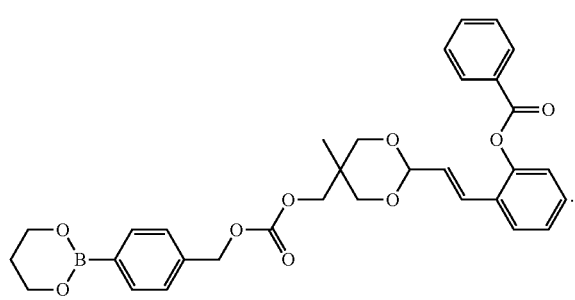 [SMILES: CC1(COC(=O)OCc2ccc(B3OCCCO3)cc2)COC(/C=C/c2ccccc2OC(=O)c2ccccc2)OC1]

5. The compound of claim 2, wherein the compound is 4-(1,3,2-dioxaborinan-2-yl)phenylmethyl-N-(5-methyl-2-styryl-1,3-dioxan-5-yl)carbamate:

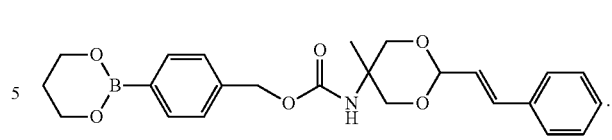

6. The compound of claim 1, wherein X is O or NH.

7. A method for preparing a compound of claim 2, comprising:

(a) preparing a cinnamaldehyde derivative having a structure

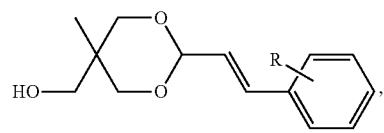

wherein R is H or $C_6H_5COO$, from a cinnamaldehyde substituted by R;

(b) preparing a compound having a structure

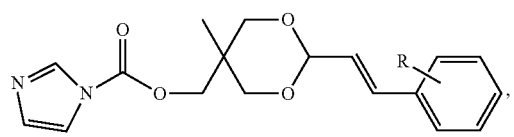

wherein R is as defined above, by reacting the cinnamaldehyde derivative prepared in step (a) with carbonyldiimidazole; and (c) reacting the compound prepared in step (b) with a boronate compound having a structure

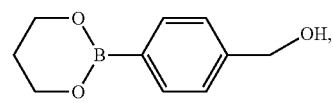 [SMILES: OCc1ccc(B2OCCCO2)cc1]

to provide the compound of claim 2.

8. A method for preparing a compound of claim 5, comprising:

(a) preparing a cinnamaldehyde derivative having a structure

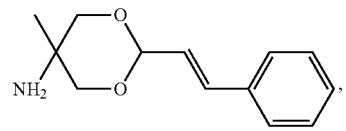

from a cinnamaldehyde;

(b) preparing a compound having a structure

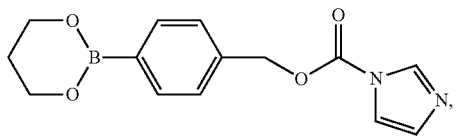 [SMILES: O=C(OCc1ccc(B2OCCCO2)cc1)n1ccnc1]

by reacting a boronate compound having a structure

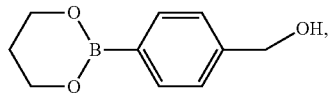

with carbonylimidazole; and
(c) reacting the cinnamaldehyde derivative prepared in step (a) with the compound prepared in step (b),
to provide the compound of claim 5.

9. A pharmaceutical composition comprising a compound of claim 2, and
a carrier, an excipient or a diluent.

10. The pharmaceutical composition of claim 9, wherein the compound is 4-(1,3,2-dioxaborinan-2-yl)benzyl((5-methyl-2-styryl-1,3-dioxan-5-yl-ethyl) carbonate:

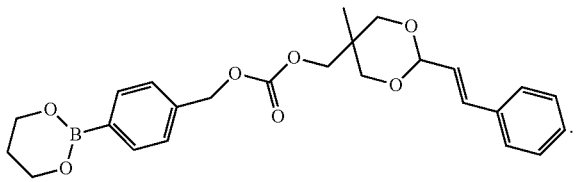 [SMILES: CC1(COC(=O)OCc2ccc(B3OCCCO3)cc2)COC(/C=C/c2ccccc2)OC1]

11. The pharmaceutical composition of claim 9, wherein the compound is 4-(1,3,2-dioxaborinan-2-yl)benzyl((5-methyl-2-(2-benzoyloxyphenyl)vinyl-1,3-dioxan-5-yl)methyl)carbonate:

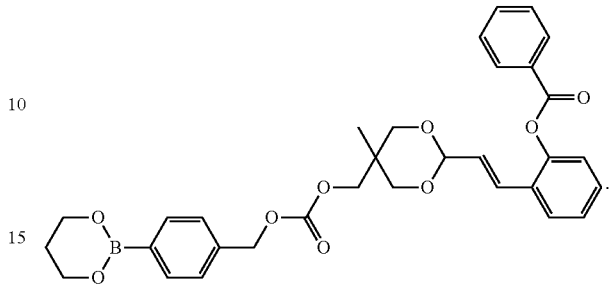

12. The pharmaceutical composition of claim 9, wherein the compound is 4-(1,3,2-dioxaborinan-2-yl)phenylmethyl-N-(5-methyl-2-styryl-1,3-dioxan-5-yl)carbamate:

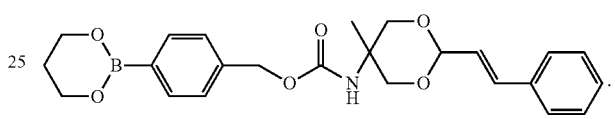

13. A method for treating cancer comprising administering to a subject in need thereof a compound of claim 2, wherein the cancer is selected from the group consisting of lung cancer, colorectal cancer, and prostate cancer.

14. A food composition comprising a compound of claim 2, and food or a food ingredient.

15. The method of claim 13, wherein the cancer is selected from the group consisting of colorectal cancer and prostate cancer.

\* \* \* \* \*